United States Patent [19]

Pierce et al.

[11] 4,348,382
[45] Sep. 7, 1982

[54] DENTIFRICE COMPOSITION

[75] Inventors: Robert C. Pierce, Plainsboro; Robert L. Mitchell, Somerset, both of N.J.

[73] Assignee: Colgate-Palmolive Company, New York, N.Y.

[21] Appl. No.: 313,046

[22] Filed: Oct. 19, 1981

Related U.S. Application Data

[63] Continuation-in-part of Ser. No. 213,423, Dec. 5, 1980, abandoned.

[51] Int. Cl.$^3$ .............................................. A61K 7/18
[52] U.S. Cl. ...................................... 424/52; 424/49; 424/57
[58] Field of Search ..................................... 424/49–58

[56]  References Cited

U.S. PATENT DOCUMENTS

| | | | |
|---|---|---|---|
| 2,647,073 | 7/1953 | Singer | 424/54 |
| 2,943,982 | 7/1960 | Dahlin | 424/57 |
| 3,308,029 | 3/1967 | Saunder et al. | 424/52 |
| 3,634,585 | 1/1972 | Manahan et al. | 424/52 |
| 3,829,562 | 8/1974 | Kim et al. | 424/57 |
| 4,169,796 | 10/1979 | Dahlin | 424/57 |

FOREIGN PATENT DOCUMENTS

| | | |
|---|---|---|
| 1435624 | 5/1976 | United Kingdom . |
| 1460581 | 1/1977 | United Kingdom . |
| 1468149 | 3/1977 | United Kingdom . |
| 1514942 | 6/1978 | United Kingdom . |
| 1530644 | 11/1978 | United Kingdom . |
| 1544537 | 4/1979 | United Kingdom . |

OTHER PUBLICATIONS

Naylor et al. Brit. Dental J. 7/4/67, pp. 17–23.
Cosmetics, Science & Technology, Balsam & Sagarin, 2nd Edition, vol. 1, pp. 477–479.

*Primary Examiner*—Shep K. Rose
*Attorney, Agent, or Firm*—Robert L. Stone; Murray M. Grill; Herbert S. Sylvester

[57]  ABSTRACT

Dentifrice composition comprising sodium monofluorophosphate and compatible polishing material, at least a major portion of which is dicalcium phosphate dihydrate having a particle size such that all particles are above 3 microns in size at at least 65% of the particles are about 3–10 microns in size.

2 Claims, No Drawings

DENTIFRICE COMPOSITION

This application is a continuation in part of Patent Application Ser. No. 213,423, filed Dec. 5, 1980, now abandoned.

This invention relates to a dentifrice composition containing sodium monofluorophosphate and a polishing material containing at least a major portion of finely divided particles of dicalcium phosphate dihydrate.

Sodium monofluorophosphate is recognized as an excellent material for dentifrice use in reducing caries formation. It has been used in commercial dentifrices.

Sodium monofluorophosphate has been demonstrated to be clinically successful in reducing caries formation when used in combination with dicalcium phosphate dihydrate polishing agent (Naylor and Emslie, British Dental Journal, July 4, 1967, pages 17–23). Such dentifrices containing sodium monofluorophosphate and dicalcium phosphate dihydrate have been the subject of U.S. Pat. Nos. 3,308,029 (Saunders et al), and 3,634,585 (Manahan et al). As indicated, these dentifrices are effective in reducing caries. Nevertheless, when a dentifrice containing sodium monofluorophosphate and dicalcium phosphate dihydrate is stored and aged, it is observed to have its retention level of fluoride reduced below optimum.

In this present invention a grade of dicalcium phosphate dihydrate is provided which results in and substantially improves fluoride retention in combination with sodium monofluorophosphate over the levels which result from use of the dicalcium phosphate dihydrate of commerce.

In the prior art, it has been suggested to use low particle size of anhydrous dicalcium phosphate in dentifrices since coarse anhydrous dicalcium phosphate may tend to scratch dental enamel. Pertinent disclosures can be found in U.S. Pat. Nos. 3,647,073 (Singer); 2,943,982 (Dahlin); 3,829,562 (Kim et al); and 4,169,796 (Dahlin). However, dicalcium phosphate dihydrate has substantially less tendency to scratch dental enamel than does anhydrous dicalcium phosphate. Under these circumstances, there was no reason to undertake special procedures such as are discussed in U.S. Pat. Nos. 2,943,982; 3,829,562, or 4,169,796 to specially classify the particle size distribution of the dihydrate.

It is an advantage of this invention that high fluoride retention in a dentifrice containing sodium monofluorophosphate and dicalcium phosphate dihydrate is attained.

Other advantages will be apparent from consideration of the following disclosure.

In accordance with certain of its aspects, this invention relates to a dentifrice composition comprising about 0.05% to about 7.6% by weight of sodium monofluorophosphate and a compatible polishing material, at least a major portion of which is dicalcium phosphate dihydrate having a particle such that all particles are above 3 microns in size and at least about 65% of the particles are 3–10 microns in size.

The sodium monofluorophosphate ($Na_2PO_3F$) is a water soluble material which releases monofluorophosphate ions in water, and it may be mixed with the polishing material in any suitable amount. Such dental preparation is compatible with suitable amounts of surface-active agents, gum, etc., as described below. The sodium monofluorophosphate as commercially available may vary considerably in purity. It may be used in any suitable purity provided that any impurities do not substantially adversely affect the desired properties. In general, the purity is desirably at least about 80%. For best results, it should be at least 85%, and preferably at least 90% by weight of sodium monofluorophosphate with the balance being primarily impurities or by-products of manufacture such as sodium fluoride, water soluble sodium phosphate salt, and the like. Expressed in another way, the sodium monofluorophosphate employed should have a total fluoride content of about 12%, preferably about 12.7%; a content of not more that 1.5%, preferably not more that 1.2% of free sodium fluoride; and a sodium monofluorophosphate content of at least 12%, preferably at least 12%, and calculated as fluorine.

The proportion of sodium monofluorophosphate in the dentifrice may be varied but should be an effective, non-toxic amount containing above 0.01% fluorine (100 p.p.m.). Suitable amounts are selected within the range of about 0.05% to a maximum of about 7.6% by weight. It is preferred that the sodium fluorophosphate salt be no more than 2%, and usually within the range of 0.05% to about 1%, by weight of the dentifrice. If desired, sodium monofluorophosphate may be mixed with an additional fluoride providing material such as sodium fluoride, potassium fluoride or stannous fluoride. When this is done, the ratio of fluoride from the monofluorophosphate to the fluoride from the other fluoride salt is about 9:1 to about 3:2.

At least a major portion (at least 50% by weight) of the polishing material is finely divided dicalcium phosphate dihydrate. Typical grades of dicalcium phosphate dihydrate used in dentifrices are described in *Cosmetics, Science and Technology*, Balsam and Sagarin, Second Edition, Volume 1, pages 477–479. Reference is made therein to a commercial grade of dicalcium phosphate in which 60% of the particles are larger than 15 microns and 3% are larger than 35 microns. In U.S. Pat. No. 3,308,029, the dicalcium phosphate dihydrate is stated to be −200 mesh; i.e., to consist of particles which pass through a sieve with holes of 74 microns × 74 microns.

Grades of dicalcium phosphate dihydrate may be obtained by art recognized techniques such as air classification, comminuting, grinding, steam jet milling and the like. Air classification is preferred. The size employed comprises all particles of at least 3 microns and at least about 65% of the particles are about 3–10 microns in size, e.g., 65–100%.

A typical technique for reducing the size of dicalcium phosphate dihydrate particles and classifying the reduced size particles is as follows:

Particle separation is effected through the action of a stream of air. The feed, consisting of a mixture of particle sizes, is dropped on a horizontal distributor plate, which is driven by a vertical shaft that also carries fan blades. The plate disperses the particles into the air stream and the fan maintains a circulation of air inside the separator. The air flows downward and then suddenly reverses to flow upward. The larger and heavier particles have sufficient momentum so that they do not follow the air, but are thrown against the inner surface of the inner cone from which they are collected and withdrawn. The smaller particles accompany the air into the annular space between the two cones, where the velocity is low enough to allow the particles to settle and be removed from the bottom of the outside cone. The foregoing process of mechanical separation is referred to as air classification.

Dicalcium phosphate dihydrate may be used as the sole polishing agent or it may be mixed with a minor amount of one or more additional dentally acceptable polishing agents which do not substantially adversely affect fluoride retention in the amounts in which they are present. Such additional polishing agents include anhydrous dicalcium phosphate (it is noted that even when anhydrous dicalcium phosphate is not separately added, there can be a tendency of the hydrated salt to partially dehydrate), calcium carbonate, silica, calcined alumina, hydrated alumina, calcium pyrophosphate, tricalcium phosphate, calcium metaphosphate and the like. Typically, when additional polishing material is present the weight ratio of dicalcium phosphate to such additional material is about 99:1 to about 65:35, usually about 25:1 to 3:1. In general, it is preferred to prepare dental cream having 40-60% polishing material with dicalcium phosphate as the main polishing ingredient and from 1 to 15% calcium carbonate in the dental cream. Other polishing materials may be added in suitable amount, if desired, such as alumina, calcium pyrophosphate, tricalcium phosphate, calcium polymetaphosphate and the like. The total content of polishing agents will be usually at least 20%, such as about 20-99% and particularly from 20-75%, preferably 40-60%, in toothpastes and at least 70% in tooth powders.

Any suitable surface active or detersive material may be included in the dentifrice compositions. Such compatible material are desirable to provide additional detersive, foaming and antibacterial properties depending upon the specific type of surface active material and are selected similarly. The detergents are water-soluble organic compounds usually, and may be anionic, non-ionic or cationic in structure. It is preferred to use the watersoluble salts of higher fatty acid monoglyceride monosulphate detergent (e.g., sodium coconut fatty acid monoglyceride monosulfate) higher alkyl sulfate (e.g., sodium lauryl sulfate) higher fatty acid esters of 1,2-dihydroxy propane sulfonate (e.g., sodium coconut fatty acid ester of 1,2-hydroxy propane sulfonate), and the like.

The various surface active material may be used in any suitable amount, generally from about 0.05 to about 10% by weight, and preferably from about 0.5 to 5% by weight of the dentifrice composition.

Substantially saturated higher aliphatic acylamides of lower aliphatic amino carboxylic acid compounds, such as those having 12 to 16 carbons in the acyl radical, and as more particularly described in the U.S. Pat. No. 2,689,170, issued Sept. 14, 1954, are quite desirable. The amino acid portion is derived generally from the lower aliphatic saturated monoamino carboxylic acids having about 2 to 6 carbons, usually the monocarboxylic acid compounds. Suitable compounds are the fatty acid amines of glycine, sarcosine, alanine, 3-amino proponic acid and valine having about 12 to 16 carbons in the acyl group. It is preferred to use the N-lauroyl myristoyl and palmitoyl sarcoside compounds.

The amide compounds may be employed in the form of the free acid or preferably as the water-soluble salts thereof, such as the alkali metal, ammonium, amine and alkoylamine salts. Specific examples thereof are sodium and potassium N-lauroyl, myristoyl and palmityol sarcosides, ammonium and ethanolamine N-lauroyl sarcosides and N-lauroyl sarcosine, and sodium N-lauroyl glycide and alanide. For convenience herein, reference to "amino carboxylic acid compound", "sarcoside", and the like refers to such compounds having a free carboxylic group of the water-soluble carboxylate salts.

Such materials are utilized in pure or substantially pure form. They should be as free as practicable from soap or similar higher fatty acid material which tends to reduce the activity of these compounds. In usual practice, the amount of such higher fatty acid material is less than 15% by weight of the amide and insufficient to substantially adversely affect it, and preferably less than about 10% of said amide material.

In accordance with the present invention, the specified combinations of ingredients may be used in any suitable preparation designed for application to the oral cavity, which preparation is referred to herein as a dentifrice composition. Such dentifrice may be in solid, liquid or paste form and include tooth pastes or dental creams, tooth powders, liquid dentifrices, tablets and the like. Such products are prepared in the usual manner. In the preparation of tooth powders, it is usually sufficient to mechanically admix the various solid ingredients.

In dental cream formulation, the liquids and solids should necessarily be proportioned to form a creamy mass of desired consistency which is extrudible from a collapsible aluminum or lead tube for example. In general, the liquids in the dental cream will comprise chiefly water, glycerine, sorbitol, propylene glycol, or the like, including suitable mixtures thereof. It is advantageous usually to use a mixture of both water and a humectant or binder such as glycerine, sorbitol or mixtures thereof. The total liquid content will generally be about 20-75% by weight of the formulation. It is preferred to use also a gelling agent in dental creams such as the natural and synthetic gums and gumlike materials, e.g., Irish Moss, gum tragacanth, sodium carboxymethyl cellulose, polyvinylpyrollidone, starch and the like. The Irish Moss and sodium carboxymethyl cellulose are compatible particularly and are preferred gelling agents. The gum content is usually in an amount up to about 10% and preferably about 0.5-5% by weight of the formulation.

Other types of dentifrice compositions will be formulated in known manner also.

A minor amount of hydrated aluminum oxide may be incorporated in the dentifrice preparation. More particularly, a dental cream having improved physical properties may be prepared from a mixture of the dicalcium phosphate dihydrate (optionally with a minor amount of calcium carbonate or anhydrous dicalcium phosphate suspended in a gel comprising water, humectant and gelling agent, with said monofluorophosphate compound and an organic non-soap synthetic detergent, and desirably a minor amount of hydrated aluminum oxide. These dental creams exhibit a superior degree of cosmetic properties and physical stability to aging for a long period of time. Resides being a minor amount polishing agent, the aluminum oxide acts as a stabilizing and modifying agent so as to eliminate or inhibit any tendency for separation or "bleeding" of the dental cream in the collapsible tube.

Suitable examples of hydrated aluminum oxide which may be employed are the forms known as alpha and beta aluminum oxide trihydrate and mixtures thereof. It is used usually in the form of fine particles of any desired particle size in the manufacture of the dental cream. In practice, it is preferred to use the alpha hydrate form of which at least about 90% of the particles pass through on a U.S. standard No. 325 mesh sieve and not more than about 5% of the particles by weight are less than 5 microns. It has been found that amounts of hydrated aluminum oxide from about ½ to about 10% by weight are most desirable.

There may be employed also various calcium and magnesium ion suppression agents for adjustment of physical properties of the composition. Suitable agents are the water-soluble inorganic polyphosphate salts, such as tetrasodium pyrophosphate or disodium diacid phrophosphate, with the partially neutralized or acid polyphosphate preferred. Other suitable agents are the alkali metal, preferably sodium salts of citric acid. In general, such compounds will be a minor amount or proportion of the formulation. The precise amount will vary depending upon the specific formulation, such as the physical characteristics of the dental cream, but will usually be from about 0.1% to about 3% by weight.

Various other materials may be incorporated in the oral preparations of this invention. Examples thereof are coloring or whitening agents, preservatives, silicones, chlorophyll compounds and ammoniated materials such as urea, diammonium phosphate and mixtures thereof. These adjuvants are incorporated in the instant compositions in amounts which do not substantially adversely affect the properties and characteristics suitably selected and used in proper amount depending upon the particular type of preparation involved.

For some purposes, it may be desirable to include antibacterial agents in the compositions of the present invention. Typical antibacterial agents which may be used in amounts of about 0.01% to about 5%, preferably about 0.05% to about 1.0% by weight of the dentifrice composition, include:
$N^1$-4-(chlorobenzyl)-$N^5$-(2,4-dichlorobenzyl) biguanide;
p-chlorophenyl biguanide;
4-chlorobenzhydryl biguanide;
4-chlorobenzhydrylguanylurea;
N-3-lauroxypropyl-$N^5$-p-chlorobenzylbiguanide;
1,6-di-p-chlorophenylbiguanidohexane;
1-(lauryldimethylammonium)-8-(p-chlorobenzyl dimethylammonium octane dichloride;
5,6-dichloro-2-guanidinobenzimidazole;
5-amino-1,3-bis(2-ethylhexyl)-5 methylhexahydropyridine;
and their non-toxic acid addition salts.

Any suitable flavoring or sweetening materials may be employed in formulating a flavor for the compositions of the present invention. Examples of suitable flavoring constituents include the flavoring oils, e.g., oils of spearmint, peppermint, wintergreen, sassafras, clove, sage, eucalyptus, marjoram, cinnamon, lemon and orange, as well as methylsalicylate. Suitable sweetening agents include sucrose, lactose, maltose, sorbitol, sodium cyclamate, sodium saccharine dipeptides of U.S. Pat. No. 3,939,261 and oxathiazin salts of U.S. Pat. No. 3,932,606. Suitably, flavor and sweetening agent may together comprise from about 0.01 to 5% or more of the instant invention.

The dental cream should have a pH practicable for use. A pH range of 5 to 9 is particularly desirable. The reference to the pH is meant to be the pH determination directly on the toothpaste. If desired, materials such as benzoic acid or citric acid may be added to adjust the pH to say 5.5 to 6.5.

The dentifrice is typically packaged in an extrudible tube, typically lined aluminum or lead or in a pressurized container.

The following specific example is further illustrative of the nature of the present invention, but it is to be understood that the invention is not limited thereto. The compositions are prepared in the usual manner and all amounts of the various ingredients are by weight unless otherwise specified.

EXAMPLE

Dicalcium phosphate dihydrate obtained from Monsanto Company as 240 C DCPD is divided into portions. One portion remains as is and another is subjected to air classification to separate particles up to 3 microns in size (7% of the number of particles). The size specifications of the 240 C DCPD control grade is as follows:

| Particle size (Microns) | % of Number of Particles smaller than indicated particle (size) |
|---|---|
| 10 | 59 |
| 5 | 23 |
| 3 | 7 |

Dicalcium phosphate dihydrate grades are formulated into the following dentifrices composition by conventional means:

|  | PARTS |
|---|---|
| Glycerine | 22.00 |
| Sodium saccharine | 0.20 |
| Sodium carboxymethyl cellulose | 1.00 |
| Sodium monofluorophosphate | 0.76 |
| Tetrasodium pyrophosphate | 0.25 |
| Dicalcium phosphate dihydrate | 48.76 |
| Sodium lauryl sulfate | 1.50 |
| Flavor | 1.00 |
| Water | 24.53 |

The following results are observed as to the soluble fluorine, soluble monofluorophosphate as fluoride and ionic fluoride after aging each dentifrice for three weeks at 49° C.:

| Grade of Dicalcium Phosphate dihydrate in Dentifrice | Soluble Fluorine (ppm) | Soluble Mono-Fluorophosphate as Fluoride (ppm) | Ionic Fluoride (ppm) |
|---|---|---|---|
| 240 C DCPD | 520 | 420 | 102 |
| Above 3 Microns | 700 | 620 | 79 |

On the basis of these results it is observed that classification of the size of dicalcium phosphate dihydrate with separation of fines below 3 microns substantially improves fluoride retention in a dentifrice containing sodium monofluorophosphate. About 65% of the particles of this grade are in a size range of about 3–10 microns.

Similar desirable results are obtained when five parts of calcium carbonate replace five parts of the classified grade of dicalcium phosphate dihydrate, and when one part of hydrated alumina also replaces one part of the classified grade of dicalcium phosphate dihydrate. Also, 0.05 parts of sodium monofluorophosphate and 0.06 parts of sodium fluoride can be used with desirable results.

The foregoing example is illustrative and modifications which are apparent to one skilled in the art may be made.

We claim:

1. A dentifrice composition with improved soluble fluorine retention comprising about 0.05% to about 7.6% by weight of sodium monofluorophosphate and about 20-99% by weight of a compatible polishing material, at least a major portion of which is dicalcium phosphate dihydrate having a particle size such that all particles are above 3 microns in size and at least about 65% of the particles are 3-10 microns in size.

2. The dentifrice composition of claim 1 wherein dicalcium phosphate dihydrate is the only polishing agent introduced into said dentifrice composition.

* * * * *